United States Patent [19]
Haynes et al.

[11] Patent Number: 5,962,112
[45] Date of Patent: *Oct. 5, 1999

[54] WIPERS COMPRISING POINT UNBONDED WEBS

[75] Inventors: Bryan David Haynes, Cumming; Laura Elizabeth Keck, Alpharetta; Charles Allen Smith, Duluth; Ty Jackson Stokes, Suwanee; David Craige Strack, Canton, all of Ga.

[73] Assignee: Kimberly-Clark Worldwide, Inc., Neenah, Wis.

[ * ] Notice: This patent is subject to a terminal disclaimer.

[21] Appl. No.: 08/769,968

[22] Filed: Dec. 19, 1996

[51] Int. Cl.⁶ .............................. B32B 3/00; B32B 27/14
[52] U.S. Cl. .................. 428/198; 428/100; 428/195; 428/219; 428/220; 428/361; 442/361; 442/381; 442/394; 604/366; 604/391
[58] Field of Search .................................... 428/198, 195, 428/100, 171, 219, 284, 286, 290, 297, 285, 903, 913, 298; 442/394, 381, 361; 604/391, 366

[56] References Cited

U.S. PATENT DOCUMENTS

| | | |
|---|---|---|
| 4,426,417 | 1/1984 | Meitner et al. .......................... 428/195 |
| 4,493,868 | 1/1985 | Meitner .................................... 428/171 |
| 4,587,154 | 5/1986 | Hotchkiss et al. ...................... 428/195 |
| 4,906,513 | 3/1990 | Kebbell et al. .......................... 428/198 |
| 5,614,281 | 3/1997 | Jackson et al. .......................... 428/100 |
| 5,683,971 | 11/1997 | Rose et al. .............................. 510/130 |
| 5,763,041 | 6/1998 | Leqak et al. ............................. 428/100 |
| 5,766,389 | 6/1998 | Brandon et al. .......................... 156/64 |

FOREIGN PATENT DOCUMENTS

| | | | |
|---|---|---|---|
| 0 080 382 | 6/1983 | European Pat. Off. ......... | D04H 1/56 |
| 2 031 039 | 4/1980 | United Kingdom ............. | D04H 1/54 |
| 96/39109 | 12/1996 | WIPO .............................. | A61F 13/15 |
| 97/24482 | 7/1997 | WIPO .............................. | D04H 1/54 |

*Primary Examiner*—Marion McCamish
*Assistant Examiner*—Arti R. Singh
*Attorney, Agent, or Firm*—James B. Robinson

[57] ABSTRACT

There is provided a wiper comprising a first web of fibers of at most 50 microns in diameter wherein said web has been bonded using a point unbonded pattern having a bond area between about 25 and 50 percent. The wiper can be made from thermoplastic polymer nonwoven fibers made by the meltblowing, spunbonding, carding and bonding, or airlaying processes. The wiper may be a laminate of various thermoplastic layers joined with the point unbonded pattern and may be a coform web of thermoplastic polymer and pulp or other material.

13 Claims, 1 Drawing Sheet

WIPERS COMPRISING POINT UNBONDED WEBS

FIELD OF THE INVENTION

This invention relates to wipers which are useful in a number of applications such as industrial cleaning wipes, food service wipes and as baby wipes.

Industrial cleaning wipes are usually saturated or impregnated with cleaning solutions which aid in the removal of oils, paints and the like. Cleaning solutions used in wipes may be "waterless", meaning water is not necessary for washing the effected area after the wipe is used. Baby wipes (or more generically, personal wipes) may be saturated with cleaning solutions as well. Either type of wipe may also contain fragrances, perfumes, and oils or other chemicals directed toward improving skin wellness, fighting bacteria or viruses, etc. Food service wipes generally must be absorbent and somewhat abrasive for cleaning surfaces. Food service wipes should also be capable of cleaning surfaces while leaving a streak free finish and without damaging the surface.

BACKGROUND OF THE INVENTION

A number of patents exist in the field of wipers, such as U.S. Pat. Nos. 4,906,513, 4,775,582, 4,659,609, 4,853,281, 4,833,003, 4,436,780, 4,298,649 and 4,778,048, commonly assigned. These patents address various attributes needed in different types of wipes as mentioned above.

There remains a need for a wipe which will be absorbent and slightly abrasive and which will have good wet texture.

SUMMARY OF THE INVENTION

The objects of this invention are achieved by a wipe produced from a web having a point unbonded pattern. The wipe may be made from nonwoven fabrics which are themselves made from a number of thermoplastics in various configurations such as conjugate and biconstituent. The wiper can be made from thermoplastic polymer nonwoven fibers made by the meltblowing, spunbonding, carding and bonding, or airlaying processes. The web may include pulp or other materials in a coform construction. The web further may be a laminate where the layers in the laminate are prebonded with the point unbonded pattern or where the layers are bonded to each other to produce the laminate using the point unbonded pattern.

DEFINITIONS

Figure 1:
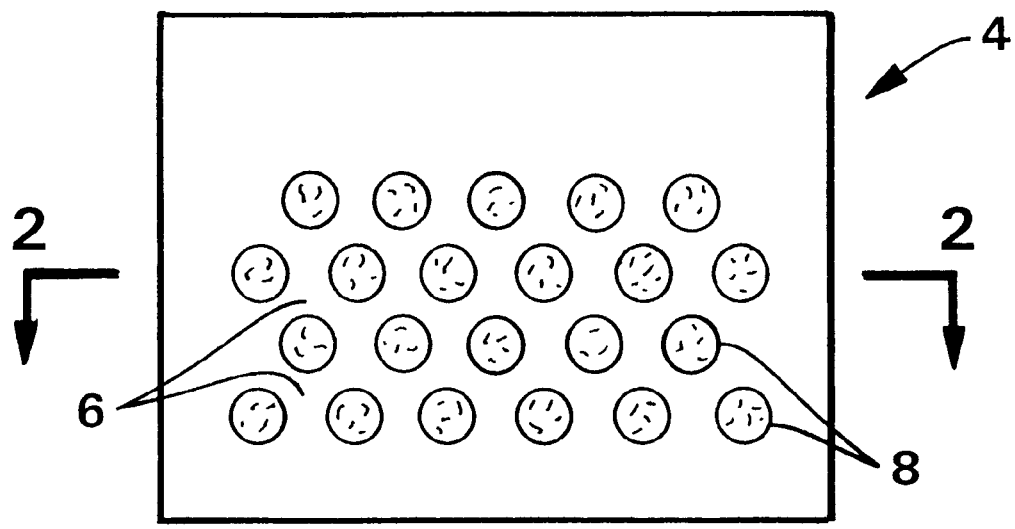
FIG. 1 is a top elevational view of the pattern-unbonded nonwoven fabric of the present invention.

"Spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 50 microns. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241. Meltblown fibers are microfibers which may be continuous or discontinuous, are generally smaller than 10 microns in average diameter, and are generally tacky when deposited onto a collecting surface.

"Conjugate fibers" refers to fibers which have been formed from at least two polymer sources extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios. The fibers may also have shapes such as those described in U.S. Pat. No. 5,277,976 to Hogle et al., and U.S. Pat. Nos. 5,069,970 and 5,057,368 to Largman et al., hereby incorporated by reference in their entirety, which describe fibers with unconventional shapes.

"Biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

As used herein, the term "machine direction" or MD means the length of a fabric in the direction in which it is produced. The term "cross machine direction" or CD means the width of fabric, i.e. a direction generally perpendicular to the MD.

As used herein, "filament arrays" means substantially parallel rows of filaments which may be such as those disclosed in U.S. Pat. Nos. 5,385,775 and 5,366,793.

As used herein "multilayer laminate" means a laminate wherein some of the layers are spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy. Multilayer laminates may also have various numbers of meltblown layers or multiple spunbond layers in many different configurations and may include other materials like films (F) or coform materials, e.g. SMMS, SM, SFS, etc.

By the term "similar web" what is meant is a web which uses essentially the same process conditions and polymers as the inventive web but in which the drawing unit is not grooved. According to Webster's New Collegiate Dictionary (1980), "similar" means 1) having characteristics in common; strictly comparable, 2) alike in substance or essentials; corresponding. Using this commonly accepted meaning of the word similar, this term means that all other conditions are essentially the same except for the conditions mentioned. It should be noted that not all conditions will be exactly identical between the different polymers since the changes in the composition itself cause process changes, in for example, the pressure drop or temperatures needed.

As used herein, the term "coform" means a process in which at least one meltblown diehead is arranged near a chute through which other materials are added to the web while it is forming. Such other materials may be pulp, superabsorbent particles, natural polymers (for example, rayon or cotton fibers) and/or synthetic polymers (for example, polypropylene or polyester) fibers, for example, where the fibers may be of staple length. Coform processes are shown in commonly assigned U.S. Pat. No. 4,818,464 to Lau and U.S. Pat. No. 4,100,324 to Anderson et al. Webs produced by the coform process are generally referred to as coform materials.

"Bonded carded web" refers to webs that are made from staple fibers which are sent through a combing or carding unit, which separates or breaks apart and aligns the staple fibers in the machine direction to form a generally machine direction-oriented fibrous nonwoven web. Such fibers are usually purchased in bales which are placed in an opener/blender or picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

"Airlaying" is a well known process by which a fibrous nonwoven layer can be formed. In the airlaying process, bundles of small fibers having typical lengths ranging from about 3 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

As used herein, the term "compaction roll" means a set of rollers above and below the web to compact the web as a way of treating a just produced microfiber, particularly spunbond, web in order to give it sufficient integrity for further processing, but not the relatively strong bonding of secondary bonding processes like through-air bonding, thermal bonding and ultrasonic bonding. Compaction rolls slightly squeeze the web in order to increase its self-adherence and thereby its integrity. Compaction rolls perform this function well but have a number of drawbacks. One such drawback is that compaction rolls do indeed compact the web, causing a decrease in bulk or loft in the web which may be undesirable for the use desired. A second and more serious drawback to compaction rolls is that the web will sometimes wrap around one or both of the rollers, causing a shutdown of the web production line for cleaning of the rollers, with the accompanying obvious loss in production during the down time. A third drawback of compaction rolls is that if a slight imperfection is produced in formation of the web, such as a drop of polymer being formed into the web, the compaction roll can force the drop into the foraminous belt, onto which most webs are formed, causing an imperfection in the belt and ruining it.

As used herein, the term "hot air knife" or HAK means a process of pre- or primarily bonding a just produced microfiber, particularly spunbond, web in order to give it sufficient integrity, i.e. increase the stiffness of the web, for further processing, but does not mean the relatively strong bonding of secondary bonding processes like TAB, thermal bonding and ultrasonic bonding. A hot air knife is a device which focuses a stream of heated air at a very high flow rate, generally from about 1000 to about 10000 feet per minute (fpm) (305 to 3050 meters per minute), or more particularly from about 3000 to 5000 feet per minute (915 to 1525 m/min.) directed at the nonwoven web immediately after its formation. The air temperature is usually in the range of the melting point of at least one of the polymers used in the web, generally between about 200 and 550° F. (93 and 290° C.) for the thermoplastic polymers commonly used in spunbonding. The control of air temperature, velocity, pressure, volume and other factors helps avoid damage to the web while increasing its integrity. The HAK's focused stream of air is arranged and directed by at least one slot of about ⅛ to 1 inches (3 to 25 mm) in width, particularly about ⅜ inch (9.4 mm), serving as the exit for the heated air towards the web, with the slot running in a substantially cross-machine direction over substantially the entire width of the web. In other embodiments, there may be a plurality of slots arranged next to each other or separated by a slight gap. The at least one slot is usually, though not essentially, continuous, and may be comprised of, for example, closely spaced holes. The HAK has a plenum to distribute and contain the heated air prior to its exiting the slot. The plenum pressure of the HAK is usually between about 1.0 and 12.0 inches of water (2 to 22 mmHg), and the HAK is positioned between about 0.25 and 10 inches and more preferably 0.75 to 3.0 inches (19 to 76 mm) above the forming wire. In a particular embodiment the HAK plenum's cross sectional area for cross-directional flow (i.e. the plenum cross sectional area in the machine direction) is at least twice the total slot exit area. Since the foraminous wire onto which spunbond polymer is formed generally moves at a high rate of speed, the time of exposure of any particular part of the web to the air discharged from the hot air knife is less a tenth of a second and generally about a hundredth of a second in contrast with the through air bonding process which has a much larger dwell time. The HAK process has a great range of variability and controllability of many factors such as air temperature, velocity, pressure, volume, slot or hole arrangement and size, and the distance from the HAK plenum to the web. The HAK is further described in U.S. patent application Ser. No. 08/362,328 to Arnold et al., filed Dec. 22, 1994 and commonly assigned.

As used herein, through-air bonding or "TAB" means a process of bonding a nonwoven bicomponent fiber web in which air which is sufficiently hot to melt one of is the polymers of which the fibers of the web are made is forced through the web. The air velocity is between 100 and 500 feet per minute and the dwell time may be as long as 6 seconds. The melting and resolidification of the polymer provides the bonding. Through air bonding has relatively restricted variability and since through-air bonding TAB requires the melting of at least one component to accomplish bonding, it is restricted to webs with two components like conjugate fibers or those which include an adhesive. In the through-air bonder, air having a temperature above the melting temperature of one component and below the melting temperature of another component is directed from a surrounding hood, through the web, and into a perforated roller supporting the web. Alternatively, the through-air bonder may be a flat arrangement wherein the air is directed vertically downward onto the web. The operating conditions of the two configurations are similar, the primary difference being the geometry of the web during bonding. The hot air melts the lower melting polymer component and thereby forms bonds between the filaments to integrate the web.

As used herein, the term "stitchbonded" means, for example, the stitching of a material in accordance with U.S. Pat. No. 4,891,957 to Strack et al. or U.S. Pat. No. 4,631,933 to Carey, Jr.

As used herein, "ultrasonic bonding" means a process performed, for example, by passing the fabric between a sonic horn and anvil roll as illustrated in U.S. Pat. No. 4,374,888 to Bornslaeger.

As used herein "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen, with about a 19% bond area. Typically, the percent bonding area varies from around 10% to around 30% of the area of the fabric laminate web. As in well known in the art, the spot bonding holds the laminate layers together as well as imparts integrity to each individual layer by bonding filaments and/or fibers within each layer.

As used herein "pattern unbonded" or interchangeably "point unbonded" or "PUB", means a fabric pattern having continuous bonded areas defining a plurality of discrete unbonded areas. The fibers or filaments within the discrete unbonded areas are dimensionally stabilized by the continuous bonded areas that encircle or surround each unbonded area, such that no support or backing layer of film or adhesive is required. The unbonded areas are specifically designed to afford spaces between fibers or filaments within the unbonded areas. A suitable process for forming the pattern-unbonded nonwoven material of this invention includes providing a nonwoven fabric or web, providing opposedly positioned first and second calender rolls and defining a nip therebetween, with at least one of said rolls being heated and having a bonding pattern on its outermost surface comprising a continuous pattern of land areas defining a plurality of discrete openings, apertures or holes, and passing the nonwoven fabric or web within the nip formed by said rolls. Each of the openings in said roll or rolls defined by the continuous land areas forms a discrete unbonded area in at least one surface of the nonwoven fabric or web in which the fibers or filaments of the web are substantially or completely unbonded. Stated alternatively, the continuous pattern of land areas in said roll or rolls forms a continuous pattern of bonded areas that define a plurality of discrete unbonded areas on at least one surface of said nonwoven fabric or web.

Figure 2:
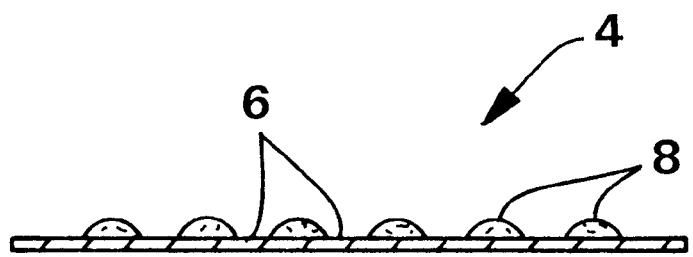
FIG. 2 is a cross-sectional side view of the pattern-unbonded nonwoven fabric of FIG. 1 taken along line 2—2.

Referring to FIGS. 1 and 2, an embodiment of the pattern-unbonded nonwoven material 4 is illustrated having continuous bonded areas 6 that define a plurality of discrete, dimensionally-stabilized unbonded areas 8. Alternative embodiments of the aforesaid process includes pre-bonding the nonwoven fabric or web before passing the fabric or web within the nip formed by the calender rolls, or providing multiple nonwoven webs to form a pattern-unbonded laminate. Pattern unbonded webs are discussed in U.S. Provisional Application 60/009,459 and subsequent regular U.S. Pat. No. 5,858,515 claiming priority from the provisional. Pattern-unbonded materials having percent bond areas ranging from about 25% to about 50%, and more particularly from about 36% to about 50%, have been found suitable.

TEST METHODS

Cup Crush: The softness of a nonwoven fabric may be measured according to the "cup crush" test. The cup crush test evaluates fabric stiffness by measuring the peak load (also called the "cup crush load" or just "cup crush") required for a 4.5 cm diameter hemispherically shaped foot to crush a 23 cm by 23 cm piece of fabric shaped into an approximately 6.5 cm diameter by 6.5 cm tall inverted cup while the cup shaped fabric is surrounded by an approximately 6.5 cm diameter cylinder to maintain a uniform deformation of the cup shaped fabric. An average of 10 readings is used. The foot and the cup are aligned to avoid contact between the cup walls and the foot which could affect the readings. The peak load is measured while the foot is descending at a rate of about 0.25 inches per second (380 mm per minute) and is measured in grams (or pounds). The cup crush test also yields a value for the total energy required to crush a sample (the "cup crush energy") which is the energy from the start of the test to the peak load point, i.e. the area under the curve formed by the load in grams on one axis and the distance the foot travels in millimeters on the other. Cup crush energy is therefore reported in gm-mm (or inch-pounds). Lower cup crush values indicate a softer laminate. A suitable device for measuring cup crush is a model FTD-G-500 load cell (500 gram range) available from the Schaevitz Company, Pennsauken, N.J..

Melt Flow Rate: The melt flow rate (MFR) is a measure of the viscosity of a polymer. The MFR is expressed as the weight of material which flows from a capillary of known dimensions under a specified load or shear rate for a measured period of time and is measured in grams/10 minutes at a set temperature and load according to, for example, ASTM test 1238-90b.

Grab Tensile test: The grab tensile test is a measure of breaking strength and elongation or strain of a fabric when subjected to unidirectional stress. This test is known in the art and conforms to the specifications of Method 5100 of the Federal Test Methods Standard 191A. The results are expressed in pounds to break and percent stretch before breakage. Higher numbers indicate a stronger, more stretchable fabric. The term "load" means the maximum load or force, expressed in units of weight, required to break or rupture the specimen in a tensile test. The term "strain" or "total energy" means the total energy under a load versus elongation curve as expressed in weight-length units. The term "elongation" means the increase in length of a specimen during a tensile test and is given in percent. Values for grab tensile strength and grab elongation are obtained using a specified width of fabric, usually 4 inches (102 mm), clamp width and a constant rate of extension. The sample is wider than the clamp to give results representative of effective strength of fibers in the clamped width combined with additional strength contributed by adjacent fibers in the fabric. The specimen is clamped in, for example, an Instron Model TM, available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154, which have 3 inch (76 mm) long parallel clamps. This closely simulates fabric stress conditions in actual use.

Material caliper (thickness or bulk): The caliper of a material is a measure of thickness and is measured at 0.05 psi with a Starret-type bulk tester, in units of millimeters.

Taber Abrasion test: This test measures the number of cycles required for an abrasion wheel to wear completely through the fabric.

DETAILED DESCRIPTION

Various woven fabrics and nonwoven webs can be used to construct a wiper. A wipe can be made from a bonded carded web or an airlaid web composed of natural and/or synthetic fibers. The bonded carded web may, for example, be a powder bonded carded web, an infrared bonded carded web, or a through-air bonded carded web. The bonded carded webs can optionally include a mixture or blend of different fibers, and the fiber lengths within a selected web may range from about 3 mm to about 60 mm.

Wipers may also be composed of nonwoven fabrics made from a variety of thermoplastic polymers where the term "thermoplastic polymer" refers to a long-chain polymer that softens when exposed to heat and returns to its original state when cooled to ambient temperature. Exemplary thermoplastics include, without limitation, poly(vinyl chloride)s, polyesters, polyamides, polyfluorocarbons, polyolefins, polyurethanes, polystyrenes, poly(vinyl alcohol)s, caprolactams, and copolymers of the foregoing, and elastomeric polymers such as elastic polyolefins, copolyether esters, polyamide polyether block copolymers, ethylene vinyl acetates (EVA), block copolymers having the general formula A—B—A' or A—B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene), A—B—A—B tetrablock copolymers and the like.

The fibers or filaments used in making pattern-unbonded nonwoven material may have any suitable morphology and may include hollow or solid, straight or crimped, single component, conjugate or biconstituent fibers or filaments, and blends or mixes of such fibers and/or filaments, as are well known in the art. All such nonwoven webs may be pre-bonded, using known nonwoven web bonding techniques such as the hot air knife, compaction rolls, through air bonding, ultrasonic bonding and stitchbonding, and subsequently bonded using the pattern-unbonded method and apparatus of the present invention, or alternatively, such nonwoven webs may only be bonded using the pattern-unbonded method and apparatus of this invention.

Many polyolefins are available for fiber production, for example polyethylenes such as Dow Chemical's ASPUN® 6811A linear low density polyethylene, 2553 LLDPE and 25355 and 12350 high density polyethylene are such suitable polymers. The polyethylenes have melt flow rates, respectively, of about 26, 40, 25 and 12. Fiber forming polypropylenes include Exxon Chemical Company's Escorene® PD 3445 polypropylene and Montell Chemical Co.'s PF-304 and PF-015. Many other conventional polyolefins are commercially available and include polybutylenes and others.

Examples of polyamides and their methods of synthesis may be found in "Polymer Resins" by Don E. Floyd (Library of Congress Catalog number 66-20811, Reinhold Publishing, New York, 1966). Particularly commercially useful polyamides are nylon-6, nylon 6,6, nylon-11 and nylon-12. These polyamides are available from a number of sources such as Emser Industries of Sumter, S.C. (Grilon® & Grilamid® nylons) and Atochem Inc. Polymers Division, of Glen Rock, N.J. (Rilsan® nylons), among others.

Useful elastomeric resins include block copolymers having the general formula A—B—A' or A—B, where A and A— are each a thermoplastic polymer endblock which contains a styrenic moiety such as a poly (vinyl arene) and where B is an elastomeric polymer midblock such as a conjugated diene or a lower alkene polymer. Block copolymers of the A—B—A' type can have different or the same thermoplastic block polymers for the A and A' blocks, and the present block copolymers are intended to embrace linear, branched and radial block copolymers. In this regard, the radial block copolymers may be designated $(A—B)_m—X$, wherein X is a polyfunctional atom or molecule and in which each $(A—B)_m—$ radiates from X in a way that A is an endblock. In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer", and particularly "A—B—A'" and "A—B" block copolymer, is intended to embrace all block copolymers having such rubbery blocks and thermoplastic blocks as discussed above, which can be extruded (e.g., by meltblowing), and without limitation as to the number of blocks. The elastomeric nonwoven web may be formed from, for example, elastomeric (polystyrene/poly (ethylene-butylene)/polystyrene) block copolymers. Commercial examples of such elastomeric copolymers are, for example, those known as KRATON® materials which are available from Shell Chemical Company of Houston, Tex. KRATON® block copolymers are available in several different formulations, a number of which are identified in U.S. Pat. Nos. 4,663,220, 4,323,534, 4,834,738, 5,093,422 and 5,304,599, hereby incorporated by reference.

Polymers composed of an elastomeric A—B—A—B tetrablock copolymer may also be used in the practice of this invention. Such polymers are discussed in U.S. Pat. No. 5,332,613 to Taylor et al. In such polymers, A is a thermoplastic polymer block and B is an isoprene monomer unit hydrogenated to substantially a poly(ethylene-propylene) monomer unit. An example of such a tetrablock copolymer is a styrene-poly(ethylene-propylene)-styrene-poly (ethylene-propylene) or SEPSEP elastomeric block copolymer available from the Shell Chemical Company of Houston, Tex. under the trade designation KRATON® G-1657.

Other exemplary elastomeric materials which may be used include polyurethane elastomeric materials such as, for example, those available under the trademark ESTANE® from B. F. Goodrich & Co. or MORTHANE® from Morton Thiokol Corp., polyester elastomeric materials such as, for example, those available under the trade designation HYTREL® from E. I. DuPont De Nemours & Company, and those known as ARNITEL®, formerly available from Akzo Plastics of Arnhem, Holland and now available from DSM of Sittard, Holland.

Another suitable material is a polyester block amide copolymer having the formula:

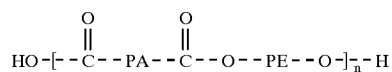

where n is a positive integer, PA represents a polyamide polymer segment and PE represents a polyether polymer segment. In particular, the polyether block amide copolymer has a melting point of from about 150° C. to about 170° C., as measured in accordance with ASTM D-789; a melt index of from about 6 grams per 10 minutes to about 25 grams per 10 minutes, as measured in accordance with ASTM D-1238, condition Q (235 C/1 Kg load); a modulus of elasticity in flexure of from about 20 Mpa to about 200 Mpa, as measured in accordance with ASTM D-790; a tensile strength at break of from about 29 Mpa to about 33 Mpa as measured in accordance with ASTM D-638 and an ultimate elongation at break of from about 500 percent to about 700 percent as measured by ASTM D-638. A particular embodiment of the polyether block amide copolymer has a melting point of about 152° C. as measured in accordance with ASTM D-789; a melt index of about 7 grams per 10 minutes, as measured in accordance with ASTM D-1238, condition Q(235 C/1 Kg load); a modulus of elasticity in flexure of about 29.50 Mpa, as measured in accordance with ASTM D-790; a tensile strength at break of about 29 Mpa, a measured in accordance with ASTM D-639; and an elongation at break of about 650 percent as measured in accordance with ASTM D-638. Such materials are available in various grades under the trade designation PEBAX® from ELF Atochem Inc. of Glen Rock, N.J.. Examples of the use of such polymers may be found in U.S. Pat. Nos. 4,724,184, 4,820,572 and 4,923,742 hereby incorporated by reference, to Killian et al. and assigned to the same assignee as this invention.

Elastomeric polymers also include copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. No. 4,803,117.

The thermoplastic copolyester elastomers include copolyetheresters having the general formula:

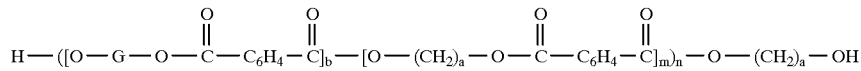

where "G" is selected from the group consisting of poly (oxyethylene)-alpha,omega-diol, poly(oxypropylene)-alpha, omega-diol, poly(oxytetramethylene)-alpha,omega-diol and "a" and "b" are positive integers including 2, 4 and 6, "m" and "n" are positive integers including 1–20. Such materials generally have an elongation at break of from about 600 percent to 750 percent when measured in accordance with ASTM D-638 and a melt point of from about 350° F. to about 400° F. (176 to 205° C.) when measured in accordance with ASTM D-2117.

Commercial examples of such copolyester materials are, for example, those known as ARNITEL®, formerly available from Akzo Plastics of Arnhem, Holland and now available from DSM of Sittard, Holland, or those known as HYTREL® which are available from E.I. DuPont de Nemours of Wilmington, Del. Formation of an elastomeric nonwoven web from polyester elastomeric materials is disclosed in, for example, U.S. Pat. No. 4,741,949 to Morman et al. and U.S. Pat. No. 4,707,398 to Boggs, hereby incorporated by reference.

Elastomeric olefin polymers are available from Exxon Chemical Company of Baytown, Tex. under the trade name ACHIEVE® for polypropylene based polymers and EXACT® and EXCEED® for polyethylene based polymers. Dow Chemical Company of Midland, Mich. has polymers commercially available under the name ENGAGE®. These materials are believed to be produced using non-stereo selective metallocene catalysts. Exxon generally refers to their metallocene catalyst technology as "single site" catalysts while Dow refers to theirs as "constrained geometry" catalysts under the name INSIGHT® to distinguish them from traditional Ziegler-Natta catalysts which have multiple reaction sites. Other manufacturers such as Fina Oil, BASF, Amoco, Hoechst and Mobil are active in this area and it is believed that the availability of polymers produced according to this technology will grow substantially in the next decade.

Wipers may be composed of a substantially hydrophobic material, and the hydrophobic material may optionally be treated with a surfactant or otherwise processed to impart a desired level of wettability and hydrophilicity. Wipers can have a generally uniform thickness and cross-sectional area. It is also possible to have other materials blended with the thermoplastics used to produce a nonwoven fabric like fluorocarbon chemicals to enhance chemical repellence which may be, for example, any of those taught in U.S. Pat. No. 5,178,931, fire retardants for increased resistance to fire and/or pigments to give each layer the same or distinct colors. Fire retardants and pigments for spunbond and meltblown thermoplastic polymers are known in the art and are internal additives. A pigment, if used, is generally present in an amount less than 5 weight percent of the web while other materials may be present in a cumulative amount less than 25 weight percent.

Webs of this invention may also have topical treatments applied to them for more specialized functions. Such topical treatments and their methods of application are known in the art and include, for example, alcohol repellence treatments, anti-static treatments and the like, applied by spraying, dipping, etc. An example of such a topical treatment is the application of Zelec® antistat (available from E.I. DuPont, Wilmington, Del.).

A wiper may be, for example, a web of fine denier (5 to 10 denier) side by side polypropylene/polyethylene conjugate fibers. Such a web may be laminated to a fine fiber (1–10 micron) polypropylene web using the point unbonded (PUB) pattern where the fine fiber web can provide liquid capacity. A laminated wiper made in this manner has shown an alcohol capacity of 500 to 600 weight percent.

Another example of a wiper is one made of pulp (or other material) and thermoplastic polymer according to the coform process defined above, using the point unbonded pattern. Such a wiper has been made with 65 weight percent of Weyerhaeuser's CF405 pulp and 35 weight percent of meltblown polypropylene (Montell Chemical Corporation's PF-015) where the wipe had a basis weight of about 72 gsm and a bond area of 36 percent. The wipe had a dry bulk (thickness or caliper) of about 0.89 cm, wet bulk of about 0.60 cm, a cup crush load of about 2970 pounds, a Taber abrasion of 22, an MD peak load of 2.08 pounds, an MD elongation of 20.7 percent, an MD energy of 0.95 inch-pounds, a CD peak load of 0.94 pounds, a CD elongation of 24.5 percent, and a CD energy of 0.51 inch-pounds. A similar coform web was made without any bonding (beyond that from the interaction of the fibers) or embossing, with a basis weight of about 72 gsm, and was found to have a dry bulk of about 1.44 cm, wet bulk of about 0.74 cm, a cup crush load of about 2450 pounds, a Taber abrasion of 14, an MD peak load of 1.82 pounds, an MD elongation of 18.8 percent, an MD energy of 0.74 inch-pounds, a CD peak load of 0.78 pounds, a CD elongation of 34.5 percent, and a CD energy of 0.61 inch-pounds. An important point to note in this example is that the surface texture was not lost after wetting out in the PUB web.

A wiper using the point unbonded pattern maintains its surface texture after wetting which is an advantage in its ability to remove, for example, BM from a baby's skin. In addition, the low spots provided by the texture provide a location for BM to accumulate while it is being wiped away.

If a coform PUB wipe were found to be too weak to effectively capture and consolidate the pulp fibers without the need for adhesives or other binders, another layer could be provided as a support layer. Support layers include spunlace or spunbond fabrics, for example, scrim materials, or any other layer which provided an acceptable level of support for the coform web. A support layer may be a center layer wherein it is surrounded by coform PUB layers on either side. The webs could be laminated together by any method known in the art.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A wiper comprising a first web of fibers of at most 50 microns in diameter wherein said web has been bonded using a point unbonded pattern having a bond area between about 36 and 50 percent and wherein said fibers have at least a portion extending into and bonding within said bond area.

2. The wiper of claim 1 comprising thermoplastic polymer nonwoven fibers made from a process selected from the group consisting of meltblowing, spunbonding, carding and bonding, and airlaying.

3. The wiper of claim 2 therein said process is spunbonding.

4. The wiper of claim 3 wherein said fibers are conjugate fibers.

5. The wiper of claim 4 wherein said conjugate fibers are comprised of polyethylene and polypropylene.

6. The wiper of claim 2 wherein said thermoplastic polymer is elastic.

7. The wiper of claim 6 wherein said elastic thermoplastic polymer is selected from the group consisting of elastic polyolefins, copolyether esters, polyamide polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene) and A—B—A—B tetrablock copolymers.

8. The wiper of claim product of claim 2 wherein said process is meltblowing.

9. The wiper of claim 8 wherein said web further comprises pulp in a coform construction.

10. The wiper of claim 2 wherein said wiper is a baby wiper.

11. The wiper of claim 2 wherein said wiper is a food service wipe.

12. The wiper of claim 2 wherein said wiper is an industrial cleaning wipe.

13. A baby wipe comprising a coform web of pulp and thermoplastic polymer fibers having an average diameter of less than 10 microns, bonded together using a point unbonded pattern having a bond area between about 36 and 50 percent and wherein said fibers have at least a portion extending into and bonding within said bond area.

* * * * *